United States Patent [19]

Chen et al.

[11] 4,090,850

[45] May 23, 1978

[54] APPARATUS FOR USE IN RADIOIMMUNOASSAYS

[75] Inventors: Ching-Hong Chen, North Brunswick; Horng-Mou Tsay, East Brunswick; Robert E. Heyer, Hopatcong, all of N.J.

[73] Assignee: E. R. Squibb & Sons, Inc., Princeton, N.J.

[21] Appl. No.: 737,250

[22] Filed: Nov. 1, 1976

[51] Int. Cl.² .................... G01N 33/16; G01N 23/00; A61K 43/00
[52] U.S. Cl. .................................. 23/259; 23/230 B; 23/230.6; 23/253 R; 23/253 TP; 424/1
[58] Field of Search .......... 23/230 B, 253 R, 253 TP, 23/259; 424/1, 1.5; 195/127

[56] References Cited

U.S. PATENT DOCUMENTS

| 3,555,143 | 1/1971 | Axen | 424/1 |
|---|---|---|---|
| 3,592,888 | 7/1971 | Wolf | 424/1 |
| 3,720,760 | 3/1973 | Bennich | 424/1 |
| 3,790,663 | 2/1974 | Garrison | 424/1 X |
| 3,826,619 | 7/1974 | Bratu | 424/1 X |
| 3,853,987 | 12/1974 | Dreyer | 424/1 |
| 3,867,517 | 2/1975 | Ling | 424/1 X |
| 4,012,494 | 3/1977 | Ling | 424/1.5 X |
| 4,038,149 | 7/1977 | Liner | 195/127 |

OTHER PUBLICATIONS

G. M. Addison et al., Hormone and Metabolic Research, vol. 3, No. 1, 59–60 (Jan. 1971).

*Primary Examiner*—Sidney Marantz
*Attorney, Agent, or Firm*—Lawrence S. Levinson; Merle J. Smith; Donald J. Barrack

[57] ABSTRACT

Antibody coated cellulose paper can be used in radioimmunoassays in conjunction with test apparatus comprising a receptacle tray with multiple wells, each of said wells having at its bottom an orifice of such size and shape as to retain liquids used in the procedure under given pressure conditions and permit the evacuation of said liquid under reduced pressure.

5 Claims, 5 Drawing Figures

APPARATUS FOR USE IN RADIOIMMUNOASSAYS

BACKGROUND OF THE INVENTION

The measurement of various body constituents by the use of radioimmunoassay techniques has achieved widespread acceptance in recent years. Exemplary of substances which can be measured by radioimmunoassay using currently available commercial kits are ACTH (adrenocorticotropin), aldosterone, angiotensin I, angiotensin II, barbiturates, cyclic AMP, cyclic GMP, digoxin, folic acid, FSH (follicle stimulating hormone), gastrin, $HB_sAg$ (hepatitis B antigen), HGH (human growth hormone), insulin, TSH (thyroid stimulating hormone), T4 (thyroxine), T3 (triiodothyronine), and vitamin B12.

Yalow and Berson, *In Vitro Procedures With Radioisotopes In Medicine*, International Atomic Energy Agency, Vienna (1970) pgs. 455 et seq., express the principle of radioimmunoassay in the following terms:

"Unlabelled antigen in unknown samples competes against labelled antigen ("tracer") for binding to antibody and thereby diminishes the binding of labelled antigen. The degree of competitive inhibition observed in unknown samples is compared with that obtained in known standard solutions for determination of concentration of antigen in unknowns."

The above-described type of radioimmunoassay procedure has come to be known as the "indirect" method of radioimmunoassay. Alternatively, the "direct" method of radioimmunoassay can be used to determine the presence or absence of a particular antigen in an unknown sample. In the "direct" method, labelled antibody is mixed with the unknown sample, which if it contains the antigen in question, will bind the labelled antibody. One particular type of "direct" radioimmunoassay, known as the "sandwich" technique, may be used for the determination of the presence of antigens which have at least two antigenic sites. The "sandwich" technique comprises adding a sample (which may or may not contain antigen) and labelled antibody to unlabelled antibody. If the sample contains antigen it will bind to the unlabelled antibody and will in turn provide a binding site for the labelled antibody.

In all radioimmunoassay procedures it is necessary to provide means for separating the bound from the free labelled tracer material. Many widely varied procedures have been developed and used; exemplary procedures are electrophoresis; chromatography; ion exchange; adsorption to dextran-coated charcoal, talc, or cellulose; and a number of solid-phase antibody techniques.

Two of the widely recognized solid-phase separation techniques comprise the covalent chemical bonding of an antibody to an insoluble polymeric substance or the physical adsorption of an antibody onto an insoluble polymeric substance; see, for example, Gurvich et al., *Nature*, 203:648 (1964); Wide et al., *Biochim. Biophys. Acta.*, 130:257 (1966); Catt et al., *Biochem. J.*, 100:31c (1966); Catt et al., *J. Lab. Clin. Med.*, 70:820 (1967); Catt et al., *Nature*, 213:285 (1967); Axen et al., *Nature*, 214:1302 (1967); Catt et al., *Science*, 158:1570 (1967); Wide et al., *Lancet*, 2:1105 (1967); Salmon et al., *J. Immunol.*, 103 (1):129 (1969); Catt, U.S. Pat. No. 3,646,346, issued Feb. 29, 1972; and Axen et al., U.S. Pat. No. 3,645,852, issued Feb. 29, 1972. The principal advantage of the solid-phase antibody separation techniques in radioimmunoassays is that they allow the isolation of bound from free labelled tracer material to be carried out by a simple washing step at the completion of the immune reaction. This washing step may in practice, however, require several manipulations by the laboratory technician.

U.S. Pat. No. 3,645,852 teaches that cyanogen halides can be used to covalently link water-soluble proteins and water-soluble peptides containing a primary or secondary amino group to a water-insoluble polymer such as cellulose. Catt et al., *J. Lab. Clin. Med.*, 70:820 (1967), discuss the use of a polymeric disc (polytetrafluoroethylene-g-isothiocyanatostyrene) coated with antibody, instead of antibody coated polymer powder, as separation means in a radioimmunoassay.

The apparatus in which radioimmunoassay test procedures are performed can be a critical factor in determining the accuracy and reproducibility of the tests. Catt, in U.S. Pat. No. 3,646,346, issued Feb. 29, 1972, combined into a single entity the apparatus in which the immunochemical reaction is run and the means for separating bound from free labelled tracer material. The solid phase system of Catt, known as the "anti-body-coated tube" system comprises coating the interior of a water-insoluble polymeric test tube with antibodies against the protein to be determined; adding to the test tube an aqeuous sample containing the protein; adding to the test tube the same protein labelled with a radioisotope; aspirating the liquid from the test tube and washing the test tube; and measuring the radiation emitted by the liquid or by the test tube.

Beall et al., in U.S. Pat. No. 3,932,141, issued Jan. 13, 1976, disclose an apparatus useful in the performance of multiple radioimmunoassay test procedures. The apparatus comprises a receptacle tray with wells; polymeric balls coated with antibody to be placed in the wells; and a holder with release mechanism to be used in depositing and removing the balls from the wells. The radioimmunoassay procedure described by Beall et al. includes the use of aspiration to remove liquids from the wells.

BRIEF DESCRIPTION OF THE INVENTION

It is an object of this invention to provide apparatus for use in radioimmunoassay test which will simplify the manipulative steps that must be carried out by the laboratory technician or other person.

It is a further object of this invention to provide apparatus for use in radioimmunoassay tests that will not only simplify the manipulative steps, but will also maintain the sensitivity which makes radioimmunoassay procedures so useful.

It is a still further object of this invention to provide an apparatus for use in radioimmunoassay tests that will obviate the need for aspiration, and thus lessen the risk of contamination from one sample to another.

These, and other objects, which will be apparent to a person of ordinary skill in the art of radioimmunoassays, are achieved by the antibody coated cellulose paper of this invention when used in conjunction with the vacuum operated test apparatus of this invention.

The test apparatus of this invention comprises a receptacle tray with multiple wells, each of said wells having at its bottom an orifice of such size and shape as to retain liquid under given pressure conditions and permit the evacuation of said liquid under reduced pressure.

The cellulose paper of this invention has antibodies chemically bound or physically adsorbed to it. The antibody coated (i.e., chemically bound or physically adsorbed) paper is of sufficient porosity to permit the flow of fluids used in the radioimmunoassay.

While the most outstanding results are achieved using the antibody coated cellulose paper and vacuum operated test apparatus in combination, the use of either, with known radioimmunoassay test apparatus or separation means produces beneficial results.

The term "antigen", as used throughout the specification, is used in its broadest sense and encompasses any substance capable of causing the formation of antibodies.

The term "cellulose", as used throughout the specification, refers to both cellulose and cellulose derivatives. Cellulose and cellulose derivatives containing at least one hydroxyl, primary amino, or secondary amino group are preferred.

DETAILED DESCRIPTION OF THE INVENTION

Antibody coated cellulose paper is useful in radioimmunoassays as the means for separating bound from free labeled tracer material. The antibody coated cellulose paper must be pervious to the liquids used during the radioimmunoassay test procedure. Furthermore, the cellulose paper must be of sufficient rigidity to allow for easy handling by laboratory technicians or other persons performing radioimmunoassay tests. This can be accomplished most conveniently by circumscribing the periphery of the paper with a plastic support. However, any type of support for the cellulose paper can be used, as long as it does not impede the flow of liquid through the antibody coated cellulose paper. If the paper used is of sufficient porosity, a sufficiently thick sheet may be used to eliminate the need for additional support.

The means for coating the cellulose paper with antibody are known in the art. Physical absorption of antibody can be achieved, for example, by merely agitating the cellulose paper in a buffered solution of antibody. The particular buffering agent will of course vary with the antibody being used. The preferred method of coating the paper comprises chemically linking the antibody to the paper. This is readily accomplished using the method of Axen et al. described in Nature, 214:1302 (1967) and U.S. Pat. No. 3,645,852, issued Feb. 29, 1972. The cellulose paper is first activated by reaction with about an equivalent weight of a cyanogen halide. The activation reaction is run in an alkaline medium at a temperature of from about 0° C to 50° C. After the cellulose paper has been activated, it is reacted with a weakly alkaline solution of antibody. Reaction temperature is not critical, and the reaction can conveniently be run at room temperature.

Figure 1:
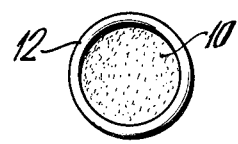
FIG. 1 is a plan view of an embodiment of the cellulose paper of this invention.

In a preferred embodiment of this invention, the cellulose paper is in the form of a disc. The most preferred embodiment of this invention, as illustrated by FIG. 1, comprises utilizing the cellulose paper 10 in the form of a disc which is circumscribed with a plastic (polystyrene has been found to be particularly useful) ring 12 to which the paper is attached. As described above, any cellulose paper of sufficient porosity to permit the passage of liquids utilized in the radioimmunoassay can be used. Tissue papers are particularly well suited for use in this invention; Kimwipes ® (Type 900-S) have been found to be most preferred.

The antibody coated cellulose paper, which is useful generally as the means for separating bound from free labelled tracer material in radioimmunoassays, is particularly useful when used in the vacuum operated test apparatus of this invention. The test apparatus of this invention comprises a receptacle tray with multiple wells, each of said wells having at its bottom an orifice of such size and shape as to retain the liquid used in a radioimmunoassay under given pressure conditions (normally this will be atmospheric pressure) and permit the evacuation of said liquid through said orifice at reduced pressure, and structure adapted to surround the outlets of said orifices with an environment of reduced pressure.

Figure 2:
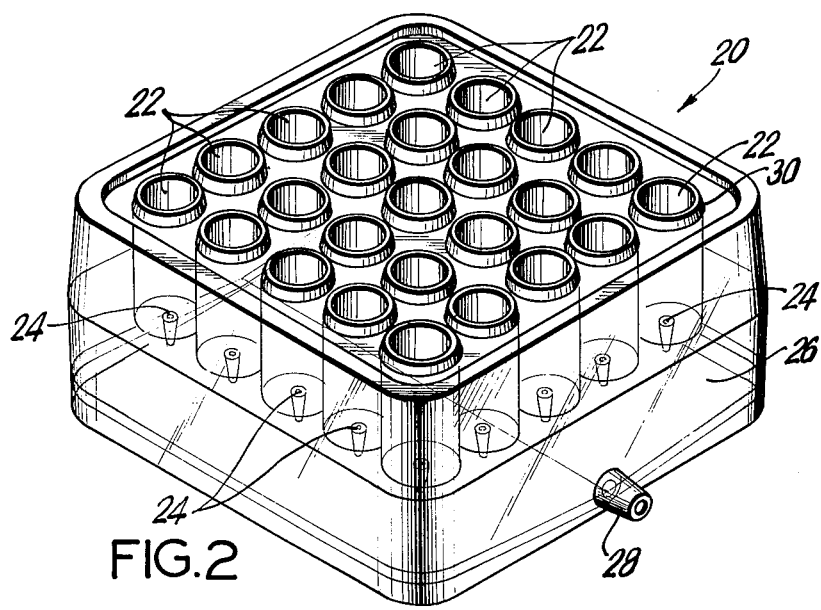
FIG. 2 is a perspective view of an embodiment of the test apparatus of this invention.
Figure 3:
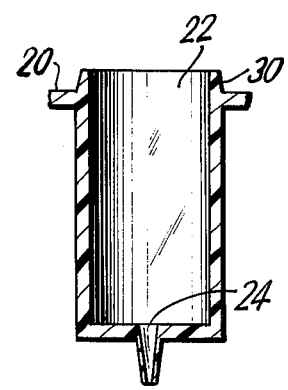
FIG. 3 is a side view in section of a well of the test apparatus of this invention.

FIG. 2 illustrates a specific embodiment of this invention. The receptacle tray 20 contains twenty-five symmetrically arranged wells 22 having an orifice 24 at the bottom of each well. The structure 26 surrounds the outlets of said orifices 24 and has means 28 to allow for the drawing of a vacuum and for the removal of the liquid from the wells. FIG. 3 is an elevational view of a well 22 and orifice 24 in cross-section. As shown in this figure, it is preferred that the wells 22 contain a lip 30 which is extended above the top of the receptacle tray. This serves to prevent accidental contamination of the contents of each well. The shape of the orifice, as shown, is an inverted conical frustrum.

Figure 4:
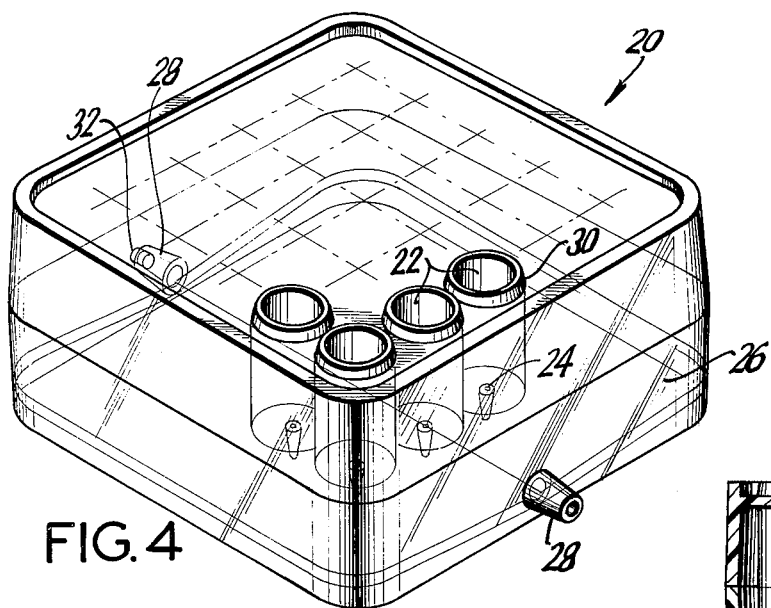
FIG. 4 is a perspective view of an alternative embodiment of the test apparatus of this invention (all wells not shown), and illustrates an apparatus having means for connecting more than one unit in series.

FIG. 4 shows an alternative embodiment of the apparatus of this invention. The structure 26 contains means 28 on two sides for drawing a vacuum. In this way, multiple receptacle trays 20 can be connected and operated in series. A plug 32 can be added at the end of the series of receptacle trays.

FIGS. 2 and 4 show the preferred shape of the test apparatus to be a rectangular prism with rounded corners which allow for easy handling.

Figure 5:
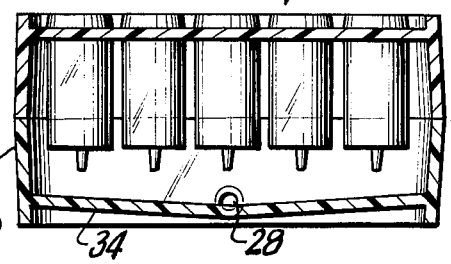
FIG. 5 is a side view in section of an embodiment of the test apparatus of this invention.

FIG. 5 shows a side cross-sectional view of the apparatus of FIG. 4. The bottom 34 of the apparatus slopes downwards from the front and back towards the middle (wherein the means 28 for drawing a vacuum is located) facilitating liquid removal.

The vacuum operated test apparatus of this invention is preferably made of moldable plastic. The plastic used may be transparent, e.g., polystyrene.

The use of antibody coated porous cellulose paper in combination with the vacuum operated test apparatus of this invention produces accurate results with a minimum of steps. Each of the wells of the vacuum operated test apparatus can contain antibody-coated cellulose paper that is pervious to the liquids used in the radioimmunoassay procedure. Unlike prior art antibody coated polymeric discs, the antibody coated cellulose paper of this invention allows liquids used in the radioimmunoassay to pass through them. Furthermore, the porous nature of the cellulose paper insures contact between the antibody coating and the antigen which may be present in the test sample and the labelled tracer material.

The vacuum operated test apparatus of this invention can be used with means for separating bound from free labelled tracer material other than antibody coated cellulose paper. For example, the wells themselves can be coated with antibody (see Catt, U.S. Pat. No. 3,646,346 issued Feb. 29, 1972) or antibody can be coated on plastic (e.g., polystyrene) beads (see Beall et al., U.S. Pat. No. 3,932,141, issued Jan. 13, 1976).

What is claimed is:

1. Apparatus for use in a radioimmunoassay test procedure comprising a receptacle tray having multiple wells, each of said wells having at its bottom an orifice of such size and shape as to retain the liquids used in the radioimmunoassay under given pressure conditions and permit the evacuation of said liquids through said orifices at reduced pressure, and structure adapted to surround the outlets of said orifices with an environment of reduced pressure.

2. Apparatus in accordance with claim 1 wherein the orifice is in the shape of an inverted conical frustrum.

3. Apparatus in accordance with claim 1 for use in a radioimmunoassay test procedure comprising a rectangular prism structure with rounded corners, having multiple wells protruding into its interior from one side, each of said wells having at its bottom an orifice of such size and shape as to retain the liquids used in the radioimmunoassay under given pressure conditions and permit the evacuation of said liquids through said orifices at reduced pressure, said structure having an orifice at or near its bottom through which air can be pulled creating an evacuated condition within the structure.

4. Apparatus for use in a radioimmunoassay test procedure comprising a receptacle tray having multiple wells, each of said wells containing an antibody coated cellulose paper that is pervious to the liquids used in the radioimmunoassay procedure and each of said wells having at its bottom an orifice of such size and shape as to retain the liquids under given pressure conditions and permit the evacuation of said liquids through said orifices at reduced pressure, and structure adapted to surround the outlets of said orifices with an environment of reduced pressure.

5. Apparatus in accordance with claim 4 wherein the antibody coated cellulose paper is in the shape of a disc and has a plastic support circumscribing its periphery.

* * * * *